(12) United States Patent
Schmitt et al.

(10) Patent No.: US 11,301,994 B2
(45) Date of Patent: Apr. 12, 2022

(54) CORONARY ARTERY HEALTH STATE PREDICTION BASED ON A MODEL AND IMAGING DATA

(71) Applicant: KONINKLIJKE PHILIPS N.V., Eindhoven (NL)

(72) Inventors: Holger Schmitt, Luetjensee (DE); Hannes Nickisch, Hamburg (DE); Tobias Wissel, Lubeck (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 106 days.

(21) Appl. No.: 16/642,253

(22) PCT Filed: Aug. 17, 2018

(86) PCT No.: PCT/EP2018/072286
§ 371 (c)(1),
(2) Date: Feb. 26, 2020

(87) PCT Pub. No.: WO2019/042789
PCT Pub. Date: Mar. 7, 2019

(65) Prior Publication Data
US 2021/0073978 A1 Mar. 11, 2021

Related U.S. Application Data

(60) Provisional application No. 62/551,812, filed on Aug. 30, 2017.

(51) Int. Cl.
*G06T 7/00* (2017.01)
*G16H 50/50* (2018.01)
(Continued)

(52) U.S. Cl.
CPC .......... *G06T 7/0012* (2013.01); *A61B 5/7275* (2013.01); *A61B 6/032* (2013.01);
(Continued)

(58) Field of Classification Search
CPC ........ G16H 50/20; G16H 30/40; G16H 50/30; G16H 50/50; A61B 5/7275; A61B 6/032;
(Continued)

(56) References Cited

U.S. PATENT DOCUMENTS

2015/0038860 A1* 2/2015 Fonte ................... A61B 6/5217
600/505
2015/0092999 A1 4/2015 Schmitt
(Continued)

FOREIGN PATENT DOCUMENTS

WO WO2015017571 A1 2/2015
WO WO2016001017 A1 1/2016

OTHER PUBLICATIONS

PCT International Search Report, International application No. PCT/EP2018/072286, dated Nov. 20, 2018.
(Continued)

*Primary Examiner* — Manuchehr Rahmjoo
(74) *Attorney, Agent, or Firm* — Larry Liberchuk

(57) ABSTRACT

A system (100) includes a computer readable storage medium (122) with computer executable instructions (124), including: a predictor (126) configured to determine a baseline coronary state and a predicted coronary state from contrast enhanced cardiac computed tomography volumetric image data and a model of an effect of one or more substances on characteristics effecting the coronary state. The system further includes a processor (120) configured to execute the predictor to determine the baseline coronary state and the predicted coronary state from the contrast enhanced cardiac computed tomography volumetric image data and the model of the effect of one or more of the substances on the characteristics effecting the coronary state. The system further includes a display configured to display the baseline coronary state and the predicted coronary state.

17 Claims, 2 Drawing Sheets

(51) Int. Cl.
| | |
|---|---|
| *G16H 50/30* | (2018.01) |
| *G16H 50/20* | (2018.01) |
| *G16H 30/40* | (2018.01) |
| *A61B 5/00* | (2006.01) |
| *A61B 6/03* | (2006.01) |
| *A61B 6/00* | (2006.01) |
| *G06T 15/08* | (2011.01) |

(52) U.S. Cl.
CPC .............. *A61B 6/503* (2013.01); *A61B 6/507* (2013.01); *G06T 15/08* (2013.01); *G16H 30/40* (2018.01); *G16H 50/20* (2018.01); *G16H 50/30* (2018.01); *G16H 50/50* (2018.01); *A61B 6/481* (2013.01); *G06T 2207/10081* (2013.01); *G06T 2207/30048* (2013.01); *G06T 2207/30104* (2013.01); *G06T 2210/41* (2013.01)

(58) Field of Classification Search
CPC ......... A61B 6/481; A61B 6/503; A61B 6/507; G06T 15/08; G06T 2207/10081; G06T 2207/30048; G06T 2207/30104; G06T 2210/41; G06T 7/0012
See application file for complete search history.

(56) References Cited

U.S. PATENT DOCUMENTS

| | | |
|---|---|---|
| 2015/0282765 A1 | 10/2015 | Goshen |
| 2016/0008084 A1 | 1/2016 | Merritt |
| 2016/0022371 A1 | 1/2016 | Sauer |
| 2016/0042144 A1 | 2/2016 | Sankaran |
| 2016/0066795 A1 | 3/2016 | Grass |
| 2017/0053092 A1 | 2/2017 | Taylor |
| 2018/0336319 A1* | 11/2018 | Itu .......................... G16H 50/70 |

OTHER PUBLICATIONS

Wolterink J.M. et al., "Automatic Coronary Artery Calcium Scoring in Cardiac CT Angiography Using Paired Convolutional Neural Networks", Medical Image Analysis 34 (2016) 123-136.

Mittal S. et al., "Fast Automatic Detection of Calcified Coronary Lesions in 3D Cardiac CT Images", In Internationa Workshop on Machine Learning in Medical Imaging (pp. 1-9), Springer Berlin Heidelberg, (Sep. 2010).

Freiman M. et al. "Improving COTA Based Lesions' Hemodynamic Significance Assessment by Accounting for Partial Volume Modeling in Automatic Coronary Lumen Segmentation", Med Phys. Mar. 2017;44(3):1040-1049.

Nickisch H. et al., "Learning Patient-Specific Lumped Models for Interactive Coronary Blood Flow Simulations", Medical Image Computing and Computer-Assisted Intervention—MICCAI 2015:18th International Conference, LNCS, 2015, vol. 9350, pp. 433-441.

Zheng Y. et al., "Robust and Accurate Coronary Artery Centerline Extraction in CTA by Combining Model-Driven and Data-Driven Approaches", Med Image Comput Assist Interv. 2013;16(Pt 3):74-81.

Ecabert O. et al., "Segmentation of the Heart and Great Vessels in CT Images Using a Model-Based Adaptation Framework", Medical Image Analysis, Dec. 2011;15(6):863-876.

Kang D. et al., "Structured Learning Algorithm for Detection of Nonobstructive and Obstructive Coronary Plaque Lesions from Computed Tomography Angiography", Journal of Medical Imaging 2(1), 014003 (Jan.-Mar. 2015).

\* cited by examiner

CORONARY ARTERY HEALTH STATE PREDICTION BASED ON A MODEL AND IMAGING DATA

FIELD OF THE INVENTION

The following generally relates to imaging and more particularly to a coronary artery health state prediction based on a model and imaging data, and finds particular application to computed tomography (CT).

BACKGROUND OF THE INVENTION

The literature indicates that in 2015 Coronary Artery Disease (CAD) affected 110 million people and resulted in 8.9 million deaths, which makes it the most common cause of death globally. CAD occurs when part of the smooth, elastic lining inside a coronary artery becomes hardened, stiffened, and swollen due to plaque buildup, which can cause a partial to full obstruction to blood flow. CAD has a number of well-determined risk factors. One such rick factor is high blood lipids. Medications that improve the health state of the coronary arteries by lowering the level of lipids in the blood and/or reversing plaque buildup in coronary arteries are available. Unfortunately, these drugs can be expensive, and taking them will not improve the health state of the coronaries arteries equally across all patients. Approaches for quantifying the hemodynamic significance of plaque include invasive and non-invasive techniques. Imaging based techniques utilize x-ray angiography or computed tomography angiography (CCTA). However, these techniques do not indicate whether a particular medication will improve the health state of the coronaries arteries.

SUMMARY OF THE INVENTION

Aspects described herein address the above-referenced problems and others.

In one aspect, a system includes a computer readable storage medium with computer executable instructions, including: a predictor configured to determine a baseline coronary state and a predicted coronary state from contrast enhanced cardiac computed tomography volumetric image data and a model of an effect of one or more substances on characteristics affecting the coronary state. The system further includes a processor configured to execute the predictor to determine the baseline coronary state and the predicted coronary state from the contrast enhanced cardiac computed tomography volumetric image data and the model of the effect of one or more of the substances on the characteristics affecting the coronary state. The system further includes a display configured to display the baseline coronary state and the predicted coronary state.

In another aspect, a computer readable storage medium is encoded with computer readable instructions, which, when executed by a computer processor of a computing system, causes the computer processor to: receive contrast enhanced cardiac computed tomography volumetric image data, obtain a model of an effect of one or more substances on characteristics affecting the coronary state, wherein the model indicates a reduction in plaque for each substance, execute a predictor to determine a baseline coronary state and a predicted coronary state from the contrast enhanced cardiac computed tomography volumetric image data and the model, display the baseline coronary state and the predicted coronary state.

In another aspect, a method includes acquiring contrast enhanced cardiac computed tomography volumetric image data, selecting a model of an effect of one or more substances on characteristics affecting the coronary state, wherein the model indicates a reduction in plaque for each substance, executing a predictor to determine a baseline coronary state and a predicted coronary state from the contrast enhanced cardiac computed tomography volumetric image data and the model, and displaying the baseline coronary state and the predicted coronary state.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
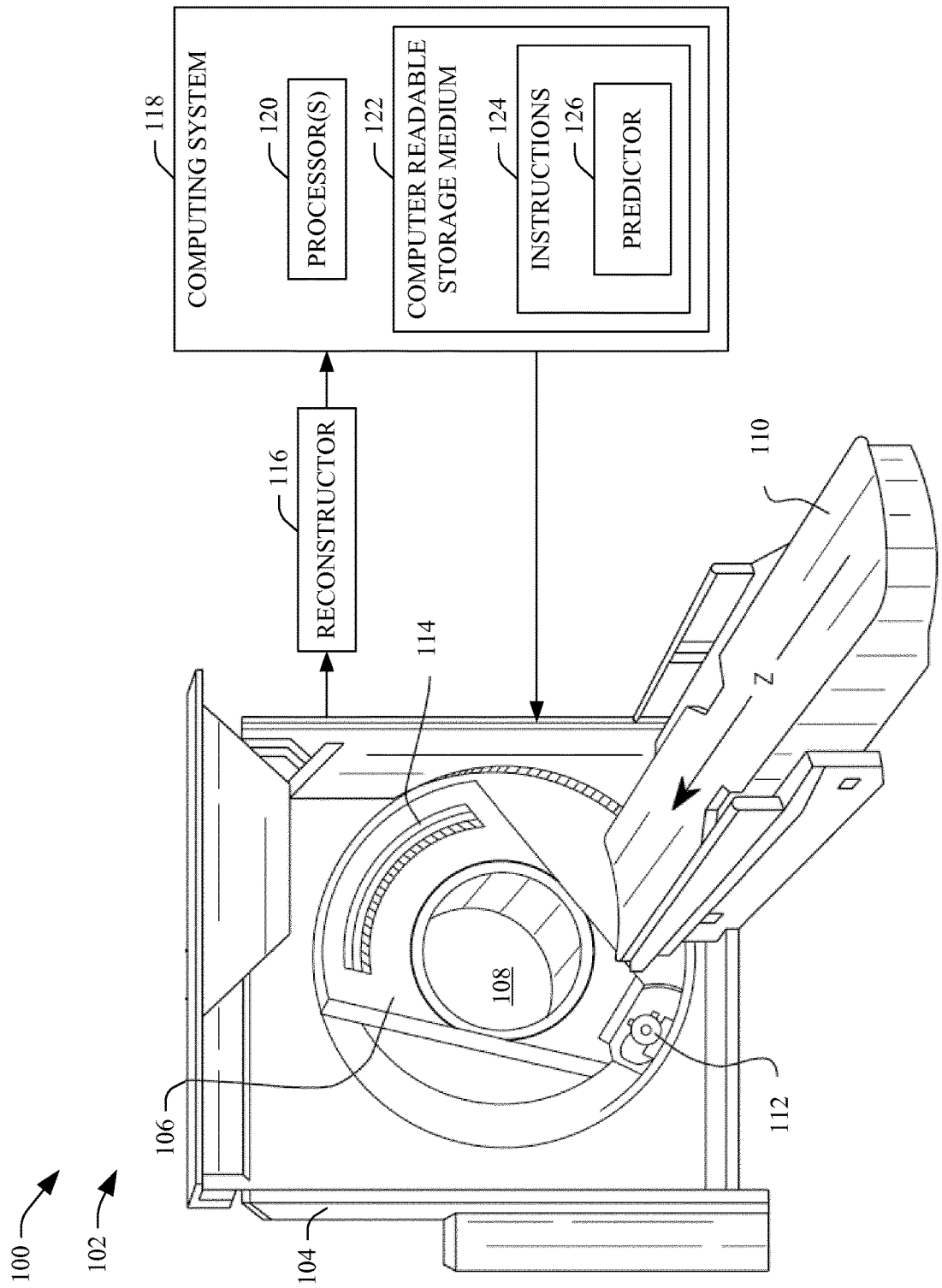
FIG. 1 schematically illustrates a system, including a computing system, with a predictor, and an imaging system.

FIG. 1 schematically illustrates a system 100 including an imaging system 102 such as a CT scanner. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108. A radiation source 112, such as an x-ray tube, is rotatably supported by the rotating gantry 106, rotates with the rotating gantry 106, and emits radiation that traverses the examination region 108.

A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof. A reconstructor 116 reconstructs the projection data, generating volumetric image data indicative of a scanned portion of a subject or object located in the examination region 108. For example, the reconstructor 116 can reconstruct CCTA image data from data acquired with a contrast enhanced CCTA scan.

A computing system 118 serves as an operator console. The console 118 includes a human readable output device such as a monitor and an input device such as a keyboard, mouse, etc. Software resident on the console 118 allows the operator to interact with and/or operate the scanner 102 via a graphical user interface (GUI) or otherwise. The console 118 further includes a processor 120 (e.g., a microprocessor, a controller, a central processing unit, etc.) and a computer readable storage medium 122, which excludes non-transitory medium, and includes transitory medium such as a physical memory device, etc.

The computer readable storage medium 122 includes instructions 124 for at least a predictor 126. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another computing system, which is separate from the computing system 118.

The predictor 126 is configured to process contrast enhanced CCTA volumetric image data and predict FFR values. This includes, in one instance, predicting FFR values for simulated changes to a state of coronary anatomy. For example, certain substances (e.g., medicines, etc.) have a physiological effect that affects the coronary anatomy when ingested or otherwise introduced into the body, and the effect may vary from person to person. The predictor 126 can predict FFR values for simulated changes to the coronary anatomy of a patient by a specific substance using a model of the effect of the specific substance. This in turn may facilitate determining whether to prescribe the specific substance to a patient.

By way of non-limiting example, substances are available which drastically lower a level of specific lipids in the blood, and which even reverse plaque buildup in coronary arteries. Examples of such substances include pro-protein convertase subtilisin/kexin type 9 inhibitors (PCSK9) such as Repatha®, a product of Amgen, Thousand Oaks, Calif., USA. These substances tend to be expensive, and taking them will not benefit all patients equally. The predictor 126 can facilitate identifying patients whose symptoms will likely be relieved and/or whose risk for acute coronary syndrome will likely be lowered by such substances, e.g., where the substance will likely lower low-density lipoprotein (LDL) cholesterol, which may reduce a risk of heart attack and/or stroke, reduce a severity of an existing stenosis, etc.

Figure 2:
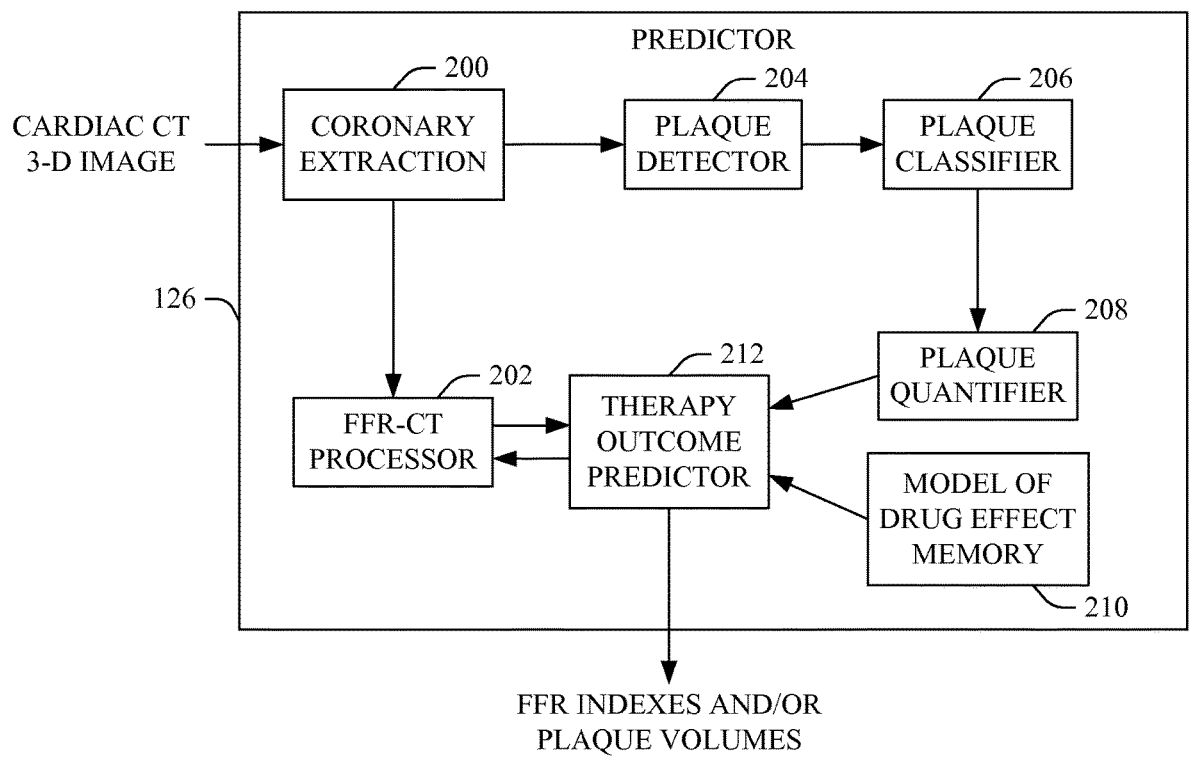
FIG. 2 schematically illustrates an example of the predictor.

FIG. 2 schematically illustrates an example of the predictor 126. The predictor 126 receives, as input, contrast enhanced CCTA volumetric image data from the imaging system 100, a data repository (e.g., a radiology information system (RIS), a picture and archiving system (PACS), etc.), and/or other apparatus.

A coronary segmentation module 200 is configured to segment a coronary tree from the contrast enhanced CCTA volumetric image data. The segmentation can be performed automatically (e.g., based on machine learning) or semi-automatically (e.g., with user assistance). In one instance, the segmentation includes identifying and/or extracting coronary artery centerlines and/or lumen geometry (e.g., diameter, perimeter, cross-sectional area, etc.) therefrom. The segmentation can be based on voxel intensity, object shape, and/or other characteristics. The output of the coronary segmentation module 200 is a segmented coronary tree and/or lumen geometry.

Examples of suitable approaches for extracting a coronary tree are discussed in Zheng et al., "Robust and accurate coronary artery centerline extraction in CTA by combining model-driven and data-driven approaches," Med Image Comput Assist Interv. 2013; 16(Pt 3):74-81, Ecabert et al., "Segmentation of the heart and great vessels in CT images using a model-based adaptation framework," Med Image Anal. 2011 December; 15(6):863-76, and Freiman et al., "Improving CCTA-based lesions' hemodynamic significance assessment by accounting for partial volume modeling in automatic coronary lumen segmentation," Med Phys. 2017 March; 44(3):1040-1049.

A FFR-CT processor 202 utilizes the segmented coronary tree and/or lumen geometry to perform a baseline FFR-CT calculation and compute a baseline FFR-CT index, which quantifies a severity of a stenosis in coronary arteries. With one approach, a parametric lumped model is employed for a patient specific computational fluid dynamic simulation of blood flow in vessel networks. The model includes a centerline representation using nonlinear resistances, with some elements indicating inflow and outflow boundary conditions, and other elements representing tree segment transfer functions, which include a series of linear and nonlinear resistance elements reflecting both the local vessel geometry and hydraulic effects. For the model, lumen geometry (e.g., diameter, perimeter, cross-sectional area) is represented by nonlinear resistors.

An example is discussed in Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. An example of deriving boundary conditions is described in EP14174891.3, filed Jun. 30, 2014, and entitled "Enhanced Patient's Specific Modelling For FFR-CT," which is incorporated herein by reference in its entirety. Examples of computing FFR values are described in US 2015/0092999 A1, filed May 10, 2013, and entitled "Determination of a fractional flow reserve (FFR) value for a stenosis of a vessel," US 2015/0282765 A1, filed Oct. 24, 2013, and entitled "Fractional flow reserve (FFR) index," which are incorporated herein by reference in their entireties.

A plaque detector module 204 detects locations of plaque along the segmented coronary arteries, e.g., based on the extracted coronary centerline and lumen. A plaque classifier module 206 classifies the detected plaque, e.g., based on the extracted coronary centerline and lumen. The detection and/or classification can be manual, e.g., by contouring and labeling voxels, or automatic, e.g., using machine learning approaches. Example classifications include lipid-rich, calcified, mixed, etc. The output of the plaque detector module 204 is the location, and the output of the plaque classifier module 206 is a type of plaque for each location.

Example approaches include Wolterink et al., "Automatic coronary artery calcium scoring in cardiac CT angiography using paired convolutional neural networks," Med Image Anal. 2016 December; 34:123-136, Kang et al., "Structured learning algorithm for detection of non-obstructive and obstructive coronary plaque lesions from coronary CT angiography," J Med Imaging. 2015; 2(1):014003, and Mittal et al., "Fast automatic detection of calcified coronary lesions in 3D cardiac CT images," In International Workshop on Machine Learning in Medical Imaging (pp. 1-9), Springer Berlin Heidelberg, (2010, September).

A plaque quantifier module 208 counts a number of labeled voxels for each type of plaque, determines a size of each plaque using the detected extent (in voxels) and the known resolution of the CT image, and quantifies each type of plaque by multiplying the corresponding number of voxels and size of a voxel for a type of plaque. The output of the plaque quantifier module 208 is a value for each type of detected plaque, the value for a particular type of plaque representing the amount or volume of that plaque in the detected plaque.

A model of drug effect memory 210 includes a model(s) that describes a likely effect of each of a plurality of different drugs on plaque. For instance, in one example the model includes a type of plaque targeted by a drug and an expected skim rate. An example for multiple drugs for the multiple plaque classifications is shown below in Table 1. For this example, the table indicates a reduction (as a percentage) of each type plaque for each drug over a predefined time period (e.g., a year). The information in the model can be based on historical outcomes of patients with plaque who were administered the particular drugs and/or simulations.

TABLE 1

Example Drug Effect Model

|  | Drug A | Drug B | ... | Drug N |
|---|---|---|---|---|
| Calcified plaque | 0% | 1% | ... | 1% |
| Lipid-rich plaque | 10% | 5% | ... | 8% |
| Mixed plaque | 7% | 5% | ... | 5% |
| . | . | . |  | . |
| . | . | . |  | . |
| . | . | . |  | . |
| Plaque M | X % | Y % | ... | Z % |

A therapy outcome predictor 212 uses the model to predict FFR indexes and/or volumes of plaque for the drugs in the model. In one instance, the therapy outcome predictor 212 applies the model to the baseline volumes of plaque computed by the plaque quantifier module 208. For instance, for "Drug A" in Table 1, the therapy outcome predictor 212 reduces the volume of calcified plaque by 0% (i.e. no reduction in this instance), reduces the volume of lipid-rich plaque by 10%, reduces the volume of mixed plaque by 7%, . . . . This produces predicted volumes of plaque for each drug in the model.

Additionally, or alternatively, the therapy outcome predictor 212 conveys the information in the model to the FFR-CT processor 202, which adjusts boundary conditions based thereon, and computes predicted FFR indexes for each drug in the model. For instance, where a boundary condition resistance is determined from a vessel diameter, the reduction in plaque increases the diameter, which reduces the boundary condition resistance; that is, resistance and diameter are inversely proportional. In this case, the FFR-CT processor 202 computes predicted FFR indexes with the adjusted boundary condition resistance.

In a variation, the plaque quantifier module 208 is omitted. In another variation, the FFR-CT processor 202 is omitted.

The output of the therapy outcome predictor 212 can include the baseline FFR index, the predicted FFR index(s), the baseline plaque volume(s), the predicted plaque volume(s), and/or differences between baseline and predicted values. For example, in one instance, the therapy outcome predictor 212 determines and displays a recommendation, such as one drug option, based on its simulated effectiveness in reducing plaque burden and/or increasing the FFR index. This can be extended to include drug induced change of blood flow/shear stress at plaque caps, take into account the size of the myocardial region at risk when a thrombus forms, etc.

The recommendation may also indicate other information such as a risk of acute coronary syndrome (ACS) with (known from the literature) and without taking each of the drugs, an improvement in myocardial perfusion based on the predicted FFR index, a monetary cost of each drug, and/or other information. For example, results for the drugs could be presented side-by-side, listing for each drug its effectiveness, cost, likelihood of adverse effects, etc. The output can be displayed via a display monitor, printed, conveyed electronically, etc. A clinician can utilize this information to determine which, if any, of the drugs to prescribe for the subject.

Figure 3:
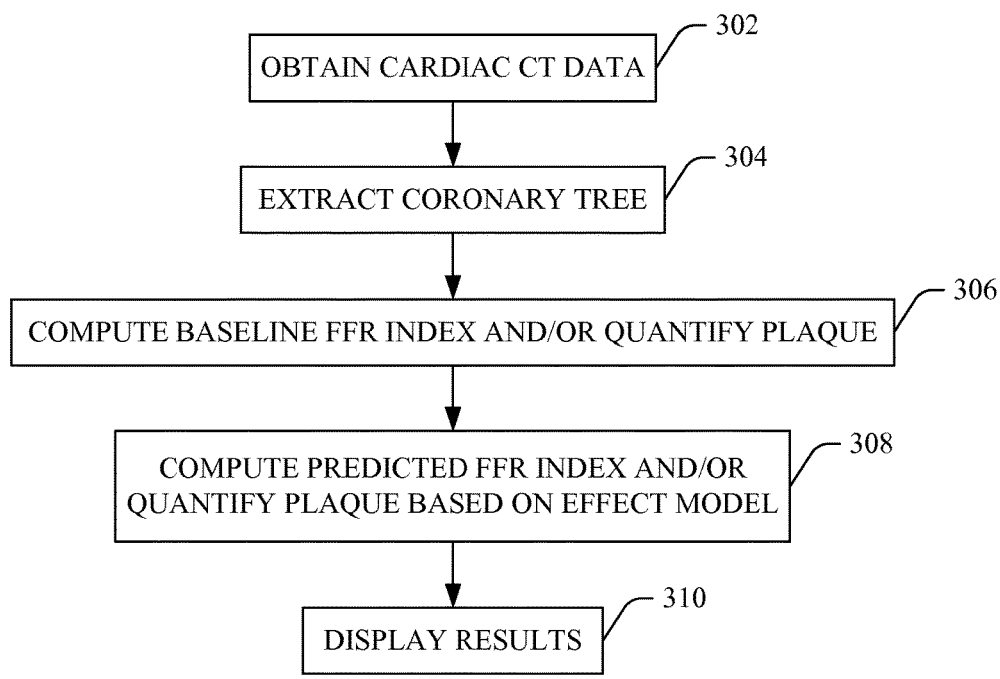
FIG. 3 illustrates an example method in accordance with an embodiment herein.

FIG. 3 illustrates an example method in accordance with an embodiment described herein.

It is to be appreciated that the ordering of the above acts is not limiting. As such, other orderings are contemplated herein. In addition, one or more acts may be omitted and/or one or more additional acts may be included.

At 302, obtain cardiac CT data of a subject.

At 304, extract a coronary tree from the cardiac CT data.

At 306, a baseline FFR index, a baseline volume of each plaque, or both are computed as described herein and/or otherwise.

At 308, a predicted FFR index, a predicted volume of each plaque, or both are computed for one or more treatment based on a model with an effect of each treatment as described herein and/or otherwise.

At 310, the results are displayed as described herein and/or otherwise.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented system, comprising:
a computer readable storage medium configured to store computer executable instructions;
a processor configured to:
segment a coronary tree from contrast enhanced cardiac computed tomography volumetric image data;
detect locations of plaque in the segmented coronary tree and classify detected plaque as a type of plague for each of the detected locations;
determine a baseline coronary state and determine a baseline volume of each of the types of plaque in the detected plaque;
determine a predicted coronary state from the contrast enhanced cardiac computed volumetric image data and a model of an effect of one or more substances on characteristics effecting the coronary state, wherein the model is applied to the baseline volume of each of the types of plaque in order to determine a predicted volume of each of the types of plaque; and a display configured to display the baseline coronary state and the predicted coronary state.

2. The system of claim 1, wherein the baseline coronary state includes a baseline fractional flow reserve index.

3. The system of claim 2, wherein the model indicates a reduction in plaque, and the predicted coronary state includes a predicted fractional flow reserve index computed based on a boundary condition determined from the reduction in the plaque.

4. The system of claim 3, wherein the processor is configured to compare baseline and predicted coronary states for each substance and indicate the substance corresponding to a largest increase in the fraction flow reserve index.

5. The system of claim 4, wherein the processor is configured to indicate an improvement in myocardial perfusion for the predicted coronary state for each of the substances.

6. The system of claim 4, wherein the processor is configured to indicate a risk of acute coronary syndrome with and without each substance.

7. The system of claim 1, wherein the types of plaque include at least one of calcified plaque, lipid-rich plaque, and mixed plaque.

8. The system of claim 1, wherein the processor is configured to compare baseline and predicted coronary states for each substance and indicate the substance corresponding to a largest decrease in volume for each type of plaque.

9. The system of claim 1, wherein the processor is configured to determine an induced change of one or more of a blood flow and a shear stress at plaque caps.

10. The system of claim 1, wherein the processor is configured to take into account a size of a myocardial region at risk when a thrombus forms.

11. A non-transitory computer readable storage medium encoded with computer readable instructions, which, when executed by a processor of a computing system, causes the processor to:
segment a coronary tree from contrast enhanced cardiac computed tomography volumetric image data;
detect locations of plaque in the segmented coronary tree and classify detected plaque as a type of plague for each of the detected locations;
determine a baseline coronary state and determine a baseline volume of each of the types of plaque in the detected plaque;
determine a predicted coronary state from the contrast enhanced cardiac computed volumetric image data and a model of an effect of one or more substances on characteristics effecting the coronary state, wherein the model is applied to the baseline volume of each of the types of plaque in order to determine a predicted volume of each of the types of plaque; and
display the baseline coronary state and the predicted coronary state.

12. The non-transitory computer readable storage medium of claim 11, wherein the baseline coronary state includes a baseline fractional flow reserve index and a baseline volume of each type of plaque.

13. The non-transitory computer readable storage medium of claim 12, wherein the processor is configured to apply the model to a boundary condition to compute the baseline fractional flow reserve index.

14. The non-transitory computer readable storage medium of claim 13, where the processor is configured to recommend a substance based on baseline and predicted fractional flow reserve indexes and volumes of each type of plaque.

15. A computer-implemented method, comprising:
segmenting a coronary tree from contrast enhanced cardiac computed tomography volumetric image data;
detecting locations of plaque in the segmented coronary tree and classifying detected plaque as a type of plaque for each of the detected locations;
determining a baseline coronary state and determining a baseline volume of each of the types of plaque in the detected plaque;
determining a predicted coronary state from the contrast enhanced cardiac computed volumetric image data and a model of an effect of one or more substances on characteristics effecting the coronary state, wherein the model is applied to the baseline volume of each of the types of plaque in order to determine a predicted volume of each of the types of plaque; and
displaying the baseline coronary state and the predicted coronary state.

16. The method of claim 15, wherein the baseline coronary state includes a baseline fractional flow reserve index and a baseline volume of each type of plaque.

17. The method of claim 16, further comprising:
applying the model to a boundary condition to compute the baseline fractional flow reserve index.

* * * * *